(12) United States Patent
Harrison et al.

(10) Patent No.: US 11,195,280 B2
(45) Date of Patent: Dec. 7, 2021

(54) PROGRESSIVE AND MULTI-PATH HOLISTICALLY NESTED NETWORKS FOR SEGMENTATION

(71) Applicant: The United States of America, as represented by the Secretary, Department of Health and Human Services, Bethesda, MD (US)

(72) Inventors: Adam Patrick Harrison, Bethesda, MD (US); Ziyue Xu, Reston, VA (US); Le Lu, Poolesville, MD (US); Ronald M. Summers, Potomac, MD (US); Daniel Joseph Mollura, Chevy Chase, MD (US)

(73) Assignee: The United States of America, As Represented by the Secretary, Department of Health and Human Services, Bethesda, MD (US)

( * ) Notice: Subject to any disclaimer, the term of this patent is extended or adjusted under 35 U.S.C. 154(b) by 26 days.

(21) Appl. No.: 16/620,464

(22) PCT Filed: Jun. 8, 2018

(86) PCT No.: PCT/US2018/036682
§ 371 (c)(1),
(2) Date: Dec. 6, 2019

(87) PCT Pub. No.: WO2018/227105
PCT Pub. Date: Dec. 13, 2018

(65) Prior Publication Data
US 2020/0184647 A1 Jun. 11, 2020

Related U.S. Application Data

(60) Provisional application No. 62/516,948, filed on Jun. 8, 2017.

(51) Int. Cl.
*G16H 50/50* (2018.01)
*G16H 30/40* (2018.01)
(Continued)

(52) U.S. Cl.
CPC .......... *G06T 7/0016* (2013.01); *A61B 5/7267* (2013.01); *A61B 6/032* (2013.01);
(Continued)

(58) Field of Classification Search
None
See application file for complete search history.

(56) References Cited

U.S. PATENT DOCUMENTS 10,140,544 B1 * 11/2018 Zhao .................. G06T 7/143
10,373,312 B2 * 8/2019 Abedini ............... G06T 7/0012
(Continued)

OTHER PUBLICATIONS

Roth H.R., Lu L., Farag A., Sohn A., Summers R.M. (2016) Spatial Aggregation of Holistically-Nested Networks for Automated Pancreas Segmentation. In: Ourselin S., Joskowicz L., Sabuncu M., Unal G., Wells W. (eds) Medical Image Computing and Computer-Assisted Intervention. vol. 9901. (Year: 2016).*
(Continued)

*Primary Examiner* — Idowu O Osifade
(74) *Attorney, Agent, or Firm* — Polsinelli PC (57) ABSTRACT

Methods include processing image data through a plurality of network stages of a progressively holistically nested convolutional neural network, wherein the processing the image data includes producing a side output from a network stage m, of the network stages, where m>1, based on a progressive combination of an activation output from the network stage m and an activation output from a preceding stage m−1. Image segmentations are produced. Systems include a 3D imaging system operable to obtain 3D imaging data for a patient including a target anatomical body, and a
(Continued)

computing system comprising a processor, memory, and software, the computing system operable to process the 3D imaging data through a plurality of progressively holistically nested convolutional neural network stages of a convolutional neural network.

27 Claims, 9 Drawing Sheets

(51) Int. Cl.

| | |
|---|---|
| *A61B 5/00* | (2006.01) |
| *A61B 6/03* | (2006.01) |
| *A61B 6/00* | (2006.01) |
| *G06N 3/04* | (2006.01) |
| *G06T 7/00* | (2017.01) |
| *G06T 7/174* | (2017.01) |
| *G06N 3/08* | (2006.01) |

(52) U.S. Cl.
CPC ............. *A61B 6/50* (2013.01); *G06N 3/0454* (2013.01); *G06N 3/0481* (2013.01); *G06N 3/084* (2013.01); *G06T 7/174* (2017.01); *G16H 30/40* (2018.01); *G16H 50/50* (2018.01); *G06T 2207/10081* (2013.01); *G06T 2207/20081* (2013.01); *G06T 2207/20084* (2013.01); *G06T 2207/30061* (2013.01)

(56) References Cited

U.S. PATENT DOCUMENTS

2019/0102897 A1* 4/2019 Lewis ................. G06T 7/12
2019/0205758 A1* 7/2019 Zhu ..................... G16H 30/40

OTHER PUBLICATIONS

Nogues I. et al. (2016) Automatic Lymph Node Cluster Segmentation Using Holistically-Nested Neural Networks and Structured Optimization in CT Images. In: Ourselin S., Joskowicz L., Sabuncu M., Unal G., Wells W. (eds) Medical Image Computing and Computer-Assisted Intervention. vol. 9901. (Year: 2016).*
Chen et al., "Semantic Image Segmentation with Deep Convolutional Nets and Fully Connected CRFs," conference paper at ICLF 2015, arXiv:1412.7062v4 [cs.CV], 14 pages (Jun. 7, 2016).
Depeursinge et al., "Building a reference multimedia database for interstitial lung diseases," *Computerized Medical Imaging and Graphics*, 36(3):227-238 (Apr. 2012).
El-Baz et al., "Computer-Aided Diagnosis Systems for Lung Cancer: Challenges and Methodologies," *Int. J. Biomedical Imaging*, 46 pages (Jan. 29, 2013).
Gill et al., "Segmentation of Lungs with Interstitial Lung Disease in CT Scans: A TV-L$^1$ Based Texture Analysis Approach," *Lecture Notes in Computer Science*, conference paper, pp. 511-520 (Dec. 2015).
Hosseini-Asl, et al., "3-D Lung Segmentation by Incremental Constrained Nonnegative Matrix Factorization," *IEEE Trans. on Biomedical Engineering*, 63(5):952-963 (May 2016).
Karwoski et al., "Processing of CT Images for Analysis of Diffuse Lung Disease in the Lung Tissue Research Consortium," *SPIE Proceedings*, vol. 6916, 9 pages (Mar. 20, 2008).
Lin et al., "RefineNet: Multi-Path Refinement Networks for High-Resolution Semantic Segmentation," arXiv:1611.06612, pp. 1925-1934 (Nov. 2016).
Long et al., "Fully Convolutional Networks for Semantic Segmentation," *Computer Vision and Pattern Recognition*, arXiv:1411.4038[cs.CV], pp. 3431-3440 (Mar. 8, 2015).
Mansoor et al., "A Generic Approach to Pathological Lung Segmentation," *IEEE Transactions on Medical Imaging*, 33(12):2293-2310 (Dec. 2014).
Nogues et al., "Automatic Lymph Node Cluster Segmentation Using Holistically-Nested Neural Networks and Structured Optimization in CT Images," Medical Image Computing and Computer-Assisted Intervention—MICCAI 2016, pp. 388-397 (Oct. 2, 2016).
Roth et al., "Spatial Aggregation of Holistically-Nested Networks for Automated Pancreas Segmentation," Medical Image Computing and Computer-Assisted Intervention—MICCAI 2016, pp. 451-459 (Oct. 2, 2016).
Sofka et al., "Multi-stage Learning for Robust Lung Segmentation in Challenging CT Volumes," Medical Image Computing and Computer-Assisted Intervention—MICCAI 2011, pp. 667-674 (Jan. 2011).
Wang et al., "Automated Segmentation of Lungs with Severe Interstitial Lung Disease in CT," *Medical Physics*, 36(10):4592-4599 (Oct. 2009).
Zhou et al., "Pancreas Segmentation in Abdominal CT Scan: A coarse-to-Fine Approach," arXiv:1612.08230vl [cs.CV], 13 pages (Dec. 25, 2016).
Çiçek, et al., "3D U-Net: Learning Dense Volumetric Segmentation from Sparse Annotation," arXiv:1606.06650v1, pp. 1-8 (Jun. 21, 2016).
International Search Report and Written Opinion for related International Application No. PCT/US2018/036682, dated Sep. 20, 2018, 11 pages.
Lee et al., "Deeply-Supervised Nets," arXiv: 1409.5185v2, pp. 562-570 (Sep. 25, 2014).
Merkow et al., "Dense Volume-to-volume Vascular Boundary Detection," *Medical Image Computing and Computer-Assisted Intervention*, pp. 1-8 (Dec. 31, 2016).
Ronneberger et al., "U-Net: Convolutional Networks for Biomedical Image Segmentation," airXiv:1505.04597v1, 8 pages (May 18, 2015).
Simonyan et al., "Very Deep Convolutional Networks for Large-Scale Image Recognition," airXiv:1409.1556v6, 14 pages (Dec. 31, 2014).
Xie et al., "Holistically-Nested Edge Detection," *IEEE International Conference on Computer Vision*, pp. 1395-1403 (Dec. 31, 2015).

\* cited by examiner

PROGRESSIVE AND MULTI-PATH HOLISTICALLY NESTED NETWORKS FOR SEGMENTATION

CROSS-REFERENCE TO RELATED APPLICATIONS

This application is the U.S. National Stage of International Application No. PCT/US2018/036682, filed Jun. 8, 2018, and claims the benefit of U.S. Provisional Application No. 62/516,948, filed Jun. 8, 2017, both of which are herein incorporated by reference in their entirety. The entire contents of U.S. patent application Ser. No. 14/971,296, filed Dec. 16, 2015, U.S. Provisional Patent Application 62/345,606, filed Jun. 3, 2016, U.S. Provisional Patent Application No. 62/450,681, filed Jan. 26, 2017, and PCT International Application No. PCT/US2017/035974, filed Jun. 5, 2017, are all incorporated by reference herein.

ACKNOWLEDGEMENT OF GOVERNMENT SUPPORT

This invention was made with support from the United States Government under project numbers Z01 CL090018 and Z01 CL040004 awarded by the National Institutes of Health, Clinical Center. The Government has certain rights in the invention.

FIELD

The field pertains to image segmentation.

BACKGROUND

Pathological lung segmentation (PLS), for example, is an important, yet challenging, medical image application due to the wide variability of pathological appearance and shape. Because PLS is often a prerequisite for other imaging analytics, methodological simplicity and generality can be important factors in usability. However, existing approaches are typically complex or do not produce sufficiently accurate or reliable image segmentations. Thus, a need remains for improvements that address the aforementioned drawbacks.

SUMMARY

Disclosed in this application are systems and methods for progressive and multi-path holistically nested neural networks for segmentation of images, such segmentation of pathological lungs or other organs, tumors, or bodies from CT images, or even segmentation objects from natural images.

According to an aspect of the disclosed technology, representative methods include processing image data through a plurality of network stages of a progressively holistically nested convolutional neural network, wherein the processing the image data includes producing a side output from a network stage m, of the network stages, where m>1, based on a progressive combination of an activation output from the network stage m and an activation output from a preceding stage m−1. In representative examples, the progressive combination is an addition of the activation output of the network stage m and the activation output of the network stage m−1. In further examples, the convolutional neural network includes at least three sequential network stages. In typical examples, each network stage includes a plurality of layers including at least a convolutional layer, a nonlinear activation layer, batch normalization layer, and a pooling layer, except a last network stage that does not include a pooling layer. In particular examples, the image data comprises a 2D section image of 3D medical imaging data, and the methods further include generating an image segmentation of an image feature in the 2D section image, the image segmentation corresponding to a mask output of a last stage of the multi-stage convolutional neural network that is based on a progressively created side output of the last stage. In training examples, methods can include training the convolutional neural network through deep supervision at each network stage by processing a set of a plurality of input training images, having respective ground truth image segmentations, through the network stages. According to some training examples, training includes, for each input training image, determining a cross-entropy loss at each network stage associated with a side output of the network stage using a class-balancing weight corresponding to an average of image segmentation edge ground truths over the set of input training images, producing an image segmentation estimate at each network stage corresponding to a mask output of the side output of the network stage, and back-propagating through the network stages with gradient descent to update network stage parameters of each network stage based on differences between the image segmentation estimates and the ground truth image segmentation of the input training image. In some examples, methods provide image segmentation of organs, tumors, or other anatomical bodies of a patient based on the image data, and the image data includes a target body. In particular examples, the target body is a pathological lung. In some pathological lung examples, the pathological lung has an infection, interstitial lung disease, or chronic obstructive pulmonary disease. In some examples, the image data is derived from one or more computerized tomography (CT) scans. In further examples, processing the image data includes classifying individual pixels or patches of the image data. In some examples, producing the side output includes applying a progressive constraint on multi-scale pathways. Some progressive constraints on multi-scale pathways can require no additional convolutional layers or network parameters. In some examples, the target is a non-anatomical object instead of an organ, tumor, or anatomical body, and the segmentation is based on natural images instead of 3D medical imaging. Further examples include a computing system including a processor and memory, the system operable to implement various example methods hereinabove. Additional examples comprise one or more non-transitory computer readable media storing computer-executable instructions, which when executed by a computer cause the computer to perform the methods examples hereinabove.

According to another aspect of the disclosed technology, systems include a 3D imaging system operable to obtain 3D imaging data for a patient including a target anatomical body, and a computing system comprising a processor, memory, and software, the computing system operable to process the 3D imaging data through a plurality of progressively holistically nested convolutional neural network stages of a convolutional neural network, including to produce a side output from a network stage m, of the network stages, where m>1, based on a progressive combination of an activation output from the network stage m and an activation output from a preceding stage m−1, and generate an image segmentation of the target anatomical body based on a progressively created mask output of a last network stage of the network stages. In some examples, the target anatomical body is a pathological lung. In particular examples, the pathological lung has an infection, interstitial lung disease, or chronic obstructive pulmonary disease. In some embodiments, the 3D imaging system comprises a computerized tomography system and the 3D imaging data is derived from one or more computerized tomography scans. In further embodiments, the computing system is operable to classify individual pixels or patches of the 3D imaging data in a bottom-up approach. In additional embodiments, the computing system is operable to apply a progressive constraint on multi-scale pathways. Some progressive constraints on multi-scale pathways can require no additional convolutional layers or network parameters. In selected examples, the progressive combination is an addition of the activation output of the network stage m and the activation output of the network stage m−1. According to representative embodiments, the computing system is operable to train the convolutional neural network through deep supervision at each network stage by processing a set of a plurality of input training images, having respective ground truth image segmentations, through the network stages. In particular examples, the computing system is operable to provide the training by, for each input training image, determining a cross-entropy loss at each network stage associated with a side output of the network stage using a class-balancing weight corresponding to an average of image segmentation edge ground truths over the set of input training images, producing an image segmentation estimate at each network stage corresponding to a mask output of the side output of the network stage, and backpropagating through the network stages with gradient descent to update network stage parameters of each network stage based on differences between the image segmentation estimates and the ground truth image segmentation of the input training image.

The foregoing and other objects, features, and advantages of the disclosed technology will become more apparent from the following detailed description, which proceeds with reference to the accompanying figures.

DETAILED DESCRIPTION

The manuscript entitled "Progressive and Multi-Path Holistically Nested Neural Networks for Pathological Lung Segmentation from CT Images," by Adam P. Harrison, Ziyue Xu, Kevin George, Le Lu, Ronald M Summers, and Daniel J. Mollura is incorporated herein by reference.

In representative examples, the technology disclosed herein comprises bottom-up deep-learning based approaches that are expressive enough to handle variations in appearance, while remaining unaffected by any variations in shape. The technology includes a deeply supervised learning framework, which is enhanced by a progressive multi-path scheme. This technology can more reliably merge outputs from different network stages, and the result can be a deep model able to produce finer detailed masks. Such deep models herein are referred to as progressive holistically-nested networks (P-HNNs). Using extensive cross-validation, the disclosed methods have been tested on large multi-institutional datasets of pathological lungs, in one exemplary application, reporting high accuracy and significant qualitative and quantitative improvements over other approaches.

Current segmentation methods, such as conventional PLS, mostly rely on top-down approaches, e.g., prior 3D shape or anatomical landmark localization. While such top-down approaches can help delineate lung areas in regions hard to discriminate, a major challenge is that all shape or localization variations usually must be accounted for, which can be extremely difficult to achieve. The technology disclosed herein employs a bottom-up problem representation to solve the limited generality of the current approaches. The disclosed technology utilizes deep-learning HNN methods, and adds a progressive multi-path enhancement that allows it to address two important limitations with standard HNNs. In general, standard HNNs are network structures guided by deep supervision on side responses. The P-HNN enhancements disclosed herein allow the disclosed methods to significantly improve segmentation performance as compared with standard HNNs. Further, representative examples of the disclosed technology do not require additional model parameters over HNNs, meaning the system can remain straightforward and simple, which can be important for usability.

This disclosed technology can be implemented as a tool that can be incorporated into an image analysis after a patient undergoes imaging, such as a thoracic CT scan. For example, soon after a patient or subject is scanned, their lung regions can be delineated and segmented using the disclosed technology, and this additional data can be included as an additional piece of data along with the original CT scan. With this, physiological measurements, such as lung volume, can be further calculated. The disclosed technology can be embodied as methods and software, as an apparatus or system, in computer readable media, or otherwise.

Figure 1:
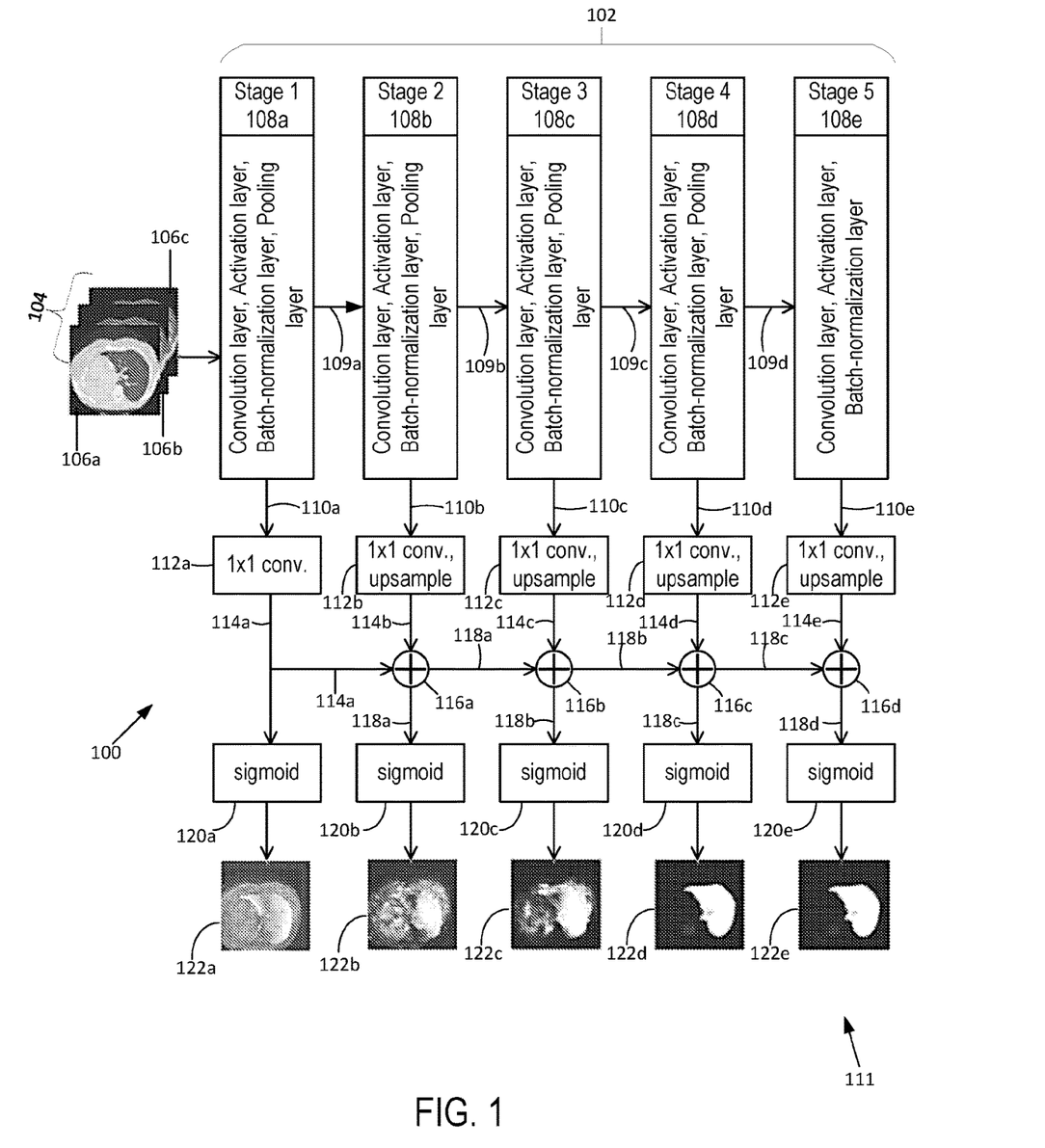
FIG. 1 is a schematic flow chart depicting methods and system examples of progressive holistically nested convolutional neural networks.

FIG. 1 is an example method 100 of image segmentation with a convolutional neural network 102 that uses multi-path enhancements to produce progressively refined deeply-supervised mask outputs at an original input resolution. In typical examples, the convolutional neural network 102 is a progressive holistically nested convolutional neural network that can be based on various neural network architectures, such as the VGG-16 model or other deep learning networks. During an image segmentation prediction, image data 104 is received, typically in the form of one or more 2D images 106a-106c, such as 2D cross-sectional images of a 3D volume image, in a computing unit containing the convolutional neural network 102. In particular examples, 3D volumes and/or 2D images correspond to images of medical targets, such as anatomical bodies, including lungs (as depicted in 2D images 106a-106c) or other organs. Images of targets can be generated using various techniques, including computed tomography, magnetic resonance, etc. The convolutional neural network includes a plurality of sequential network stages 108a-108e through which the images 106a-106c are separately processed. For convenience, processing of the image 106a is described hereinafter. In representative examples, each of the network stages 108a-108d includes a convolution layer, an activation layer, a batch-normalization layer, and a pooling layer, and the last network stage 108e includes a convolution layer, an activation layer, and a batch-normalization layer. Other layers can be included as well, such as dropout layers, etc. Convolution layers typically apply a convolution operation to the image 106a by scanning a corresponding filter set of trained weights of a predetermined size (e.g., 3×3×2 corresponding to a 3×3 pixel area and 2 colors, 10×10×2, etc.) across the image 106a. Activation layers typically apply a non-linear activation function (e.g., ReLu, softplus, sigmoid, Tanh, Leaky ReLu, etc.) to the output of the convolution layer to provide training capability within a reasonable number of iterations and/or to increase model expressivity in deep learning. Batch-normalization layers typically normalize network stage outputs and can assist with training of the convolutional neural network 102 by improving convergence times or training iterations. Pooling layers typically downsample the spatial extent of the processed slice of image data by discarding selected activations, typically without varying a depth of the processed slice of image data. After pooling, stage outputs 109a-109d are passed to respective subsequent network stages 108b-108e. During image segmentation prediction on non-training sets, one or more layers or operations can be disabled or adjusted (e.g., batch normalization, dropout layers, etc.). For example, batch normalization layers in a prediction mode can be configured to use a mean/average that is learned over a one or more training phases.

Each of the network stages 108a-108e also includes a respective activation side output 110a-110e. In typical examples, the convolutional neural network 102 does not include a fully connected layer as a last network stage, and the activation side output 110e of the last network stage 108e can be used to produce a progressive image segmentation prediction output 111 of the convolutional neural network 102. The activation side outputs 110a-110e are processed through respective 1×1 convolution stages 112a-112e that typically operate to reduce the filter dimensionality of the respective activation side outputs 110a-110e, producing convolved activation side outputs 114a-114e. As network stages 108b-108e subsequent to the first network stage 108a typically examine increasingly smaller scales, each of the 1×1 convolution stages 112b-112e include up-sampling to the resolution of input image 106a.

In representative embodiments, each of the convolved activation side outputs 114b-114e after the network stage 108a are subject to a progressive constraint by being summed at summing blocks 116a-116d with a respective convolved activation side output 114a or progressively convolved and summed activation side output 118a-118c of a respective preceding network stage. In some examples, other progressive constraints can be applied such as different arithmetic operators, combining different stage outputs, etc. The convolved activation side output 114a and the progressively convolved and summed activation side outputs 118a-118d can also be directed through respective sigmoids 120a-120e to produce mask outputs 122a-122e that correspond to image segmentation predictions for the input image 106a at each of the respective network stages 108a-108e.

The mask outputs 122b-122e are produced based on a progressive combination of the respective convolved activation side outputs 114b-114e and the respective preceding activation side outputs 114a, 118a-118c. In this way, subsequent network stages 108b-108e use a prior output as a starting point or anchor so that network stages for improvement upon previous stage outputs. In representative examples, the progressive image segmentation prediction output 111 for the input image 106a corresponds to the progressively created mask output 122e, so the mask outputs 122a-122d are not necessarily computed or displayed.

In general, in order to produce reliable image segmentation predictions, the convolution neural network 102 is trained with one or more sets of input images. For example, training data can be denoted as $S=\{(X_n,Y_n), n=1 \ldots, N\}$, where $X_n$ represents the input training images and $Y_n=\{y^{(n)}_j, j=1 \ldots, |X_n|\}$, $y^{(n)}_j \in \{0, 1\}$ represents the binary ground-truth images, i.e., correct image segmentations. Network parameters for the layers of the different network stages 108a-108e are denoted as W. During training, deep supervision is used to compute the side outputs 110a-110e, and respective losses in the form of cross-entropy loss, at the intermediate network stages 108a-108e. For example, a set of 1×1 convolutional weights $w=(w^{(1)}, \ldots w^{(m)})$ are used at the 1×1 convolution stages 112a-112e to collapse the respective activation side outputs 110a-110e, corresponding to final maps of each stage, into an image, $a^{(n,m)}_j$ for stage m, input training image n, and pixel location j. After upsampling to the original resolution of the input training image n, mask outputs 122a-122e at the intermediate stages 108a-108e are estimated using $$Pr(y_j=1|X;W,w^{(m)})=\hat{y}^{(n,m)}_j, \quad (1)$$

$$\hat{y}^{(n,m)}_j=\sigma(a^{(n,m)}_j), \quad (2)$$

$$\hat{Y}_{n,m}=\{\hat{y}^{(n,m)}_j, j=1 \ldots |X_n|\}, \quad (3)$$

where $\sigma(.)$ denotes the sigmoid function and $\hat{y}^{(n,m)}_j$ and $\hat{Y}_{n,m}$ represent the pixel- and image-level estimates, respectively. The cross-entropy loss at each side-output can then be calculated using $$\ell^{(m)}(W, w^{(m)}) = -\beta \sum_{j \in Y_+} \log \hat{y}^{(m)}_j - (1-\beta) \sum_{j \in Y_-} \log(1-\hat{y}^{(m)}_j), \quad (4)$$

where $\beta=\text{mean}(|Y_-|/|Y|)$ represents a constant and global class-balancing weight. The use of an average departs from Xie et al.'s (Xie, S., Tu, Z.: Holistically-nested edge detection. In: The IEEE International Conference on Computer Vision (ICCV) (December 2015), incorporated by reference herein) image-specific class-balancing scheme. Also, Xie et al. uses a standard holistically nested network (HNN) to output a final fused probability map based on a learned weighted sum of $\{\hat{Y}_1, \ldots \hat{Y}_m\}$. In typical examples herein, backpropagation through the multiple channels of the network stages 108a-108e is performed with gradient descent, or another suitable neural network backpropagation and update approach, to update network stage parameters W for each network stage based on differences between the image segmentation estimates $\hat{Y}_{n,m}$ and the ground truth image segmentations $Y_n$ of the input training images $X_n$. Thus, cross-entropy loss can be calculated by comparing mask outputs to ground truth masks. Such calculations can be performed after sigmoid values are determined, or based on mathematical derivations that can directly use the equivalent activations before sigmoid values are determined (e.g., to streamline numerical methods). Thus, in P-HNN examples, training gradients flow over more paths than HNN examples, as side outputs build off of prior side outputs.

Xie's holistically nested networks are powerful but include certain disadvantages, including an inconsistency of the fused output, where certain side outputs can sometimes provide superior image segmentation results, as compared to the related ground-truth, than the final fused output of the holistically nested network. This is shown by Xie et al.'s selecting different side outputs for use depending on the input dataset. In examples herein, the use of progressive constraints can provide a consistent output for use. Another issue is also one typically found in other fully convolutional neural networks where the capture of fine-level details is hampered with use of multiple stages because deeper stages have greater levels of abstraction with corresponding activations that are also coarser in spatial resolution (i.e., a down-sampling fine-to-coarse pathway associated with pooling). Approaches to address this latter issue typically use multi-path connections, such as shown in (1) Cicek, O., Abdulkadir, A., Lienkamp, S. S., Brox, T., Ronneberger, O.: 3D U-Net: Learning Dense Volumetric Segmentation from Sparse Annotation, pp. 424-432. MICCAI (2016), (2) Lin, G., Milan, A., Shen, C., Reid, I.: RefineNet: Multi-path refinement networks for high-resolution semantic segmentation. arXiv:1611.06612 (November 2016), and (3) Merkow, J., Marsden, A., Kriegman, D., Tu, Z.: Dense Volume-to-Volume Vascular Boundary Detection, pp. 371-379. MICCAI, Cham (2016). However, such approaches typically use additional and complex, coarse-to-fine pathways combining activations from earlier stages with those of later ones, e.g., such as the ubiquitous U-like structure of the neural networks in (1) Cicek, (2) Lin, and (3) Merkow. For example, (1) Cicek and (3) Merkow use multiple convolutional layers, with (3) Merkow using a three-stage training process and an extra coarse-to-fine pathway, and (2) Lin uses sub-networks to combine activations. While the approaches in (1) Cicek, (2) Lin, and (3) Merkow exhibit certain respective degrees of effectiveness, their additional network layers require extra parameters totaling nearly the same number as the original downsample convolutional neural network path, as with (1) Cicek and (3) Merkow, or more than the original convolutional neural network path, as with (2) Lin. Representative examples described herein use more straightforward progressive multi-path connections. As discussed hereinabove, progressive combinations of activations from the current and previous stages use simple addition prior to applying a sigmoid function. In typical embodiments herein, the holistically nested network approach is modified with a progressive constraint so that $$\hat{y}^{(m)}_j = \sigma(a^{(m)}_j + a^{(m-1)}_j) \forall m > 1 \quad (5)$$

As activations from different stages 108a-108e for various input images can exhibit negative or positive values, (5) forces activation side outputs 110b-110e to progressively improve upon preceding outputs, by adding to or subtracting from the corresponding activation, to make the convolutional neural network 102 into a progressive holistically-nested network (P-HNN). In representative examples, such progressive enhancements allow P-HNNs to jettison the fused output of typical HNNs, and also avoids inconsistency in the output associated with HNNs. In some examples herein, deep supervision and multi-path connections can be combined together with no extra parameters, and, in some examples, can even require fewer parameters than typical HNNs. Thus, unlike other HNN approaches, examples herein can provide enhanced new capabilities that are realized with minimal complexity.

Implementation Example

In a particular implementation example, a progressive holistically nested convolutional neural network was trained and tested on 2D axial computed tomography (CT) slices, using three windows of [−1000, 200], [−160, 240], and [−1000, −775] HUs to rescale each slice to a 3-channel 8-bit image. Typically, 3D fully convolutional neural networks rely on numerous sliding boxes, each with a limited field-of-view. Because lung regions usually occupy significant portions of a CT image, large spatial contexts may assist accurate segmentation. In addition, due to memory and computational constraints, 3D CNN models are often less deep and wide than 2D variants. Moreover, 2D CT slices can be sufficiently expressive to allow state-of-the-art performance on segmenting complex organs. Also, inter-slice thickness ranges of datasets that are acquired under low-dose scanning protocols, e.g., the University Hospitals of Geneva (UHG) dataset, can range from 5 mm to 10 mm. Associated spatial discontinuities across CT slices could severely challenge 3D shape- or CNN-based methods. In contrast, some 2D P-HNN examples can work well for any inter-slice thickness, which can be advantageous for low-dose CT scans. Thus, in this particular implementation example, a 2D approach was used that also does not require a reduction in CNN field-of-view, depth, and width.

Experimental Validation

The implementation example discussed above was validated using multi-institutional datasets from the Lung Tissue Research Consortium (LTRC) ILD/COPD dataset, the UHG ILD dataset, and a subset of an infection-based dataset collected at the National Institutes of Health (NIH) Clinical Center. LTRC image segmentation masks were initially generated using an automatic method, followed by visual inspection and manual correction if necessary. For all datasets, scan/mask pairs were visually inspected and excluded with annotation errors, resulting in in 773, 73, and 83 CT scans from the LTRC, UHG and NIH datasets, respectively. Scans included a variety of challenging patterns related to ILD, COPD, and infection.

Using five-fold cross-validation (CV), separated at the patient and dataset level, the convolutional neural network of the implementation example was trained on every tenth slice of the LTRC dataset and all slices of the other two, resulting in 38,476 training images. The convolutional neural network was fine-tuned from the ImageNet pre-trained VGG-16 model. Mini-batch size was 40 and training converged at 13,000 iterations, or roughly 13.5 epochs. Validation subsets determined probability-map thresholds. Post-processing image segmentation masks filled any 3D holes and kept the largest two connected components (e.g., first and second lungs) if the volume ratio between the two is less than 5, otherwise only the largest was kept. Depending on the number of slices, the implementation example took roughly 10 to 30 seconds to segment one volume using a Tesla K40.

Figure 2A:
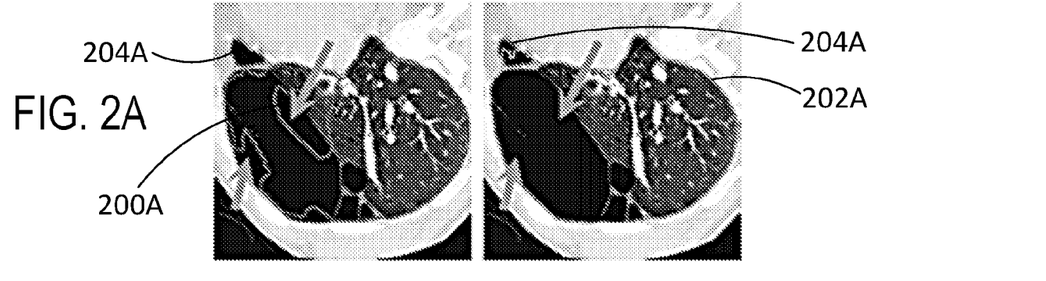
FIGS. 2A-2E are images of mask outputs of holistically nested network approaches and progressive holistically nested network examples.
Figure 2B:
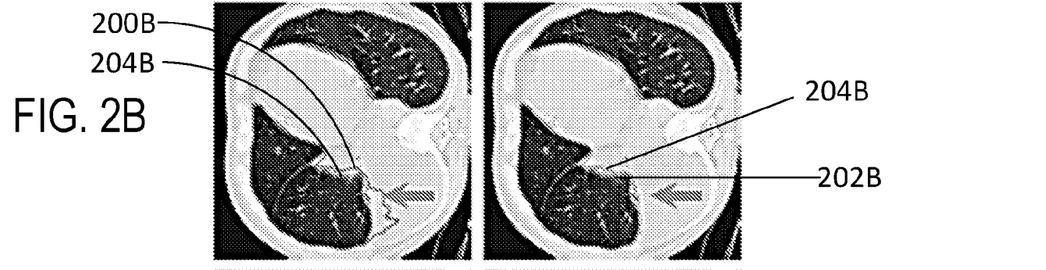
Figure 2C:
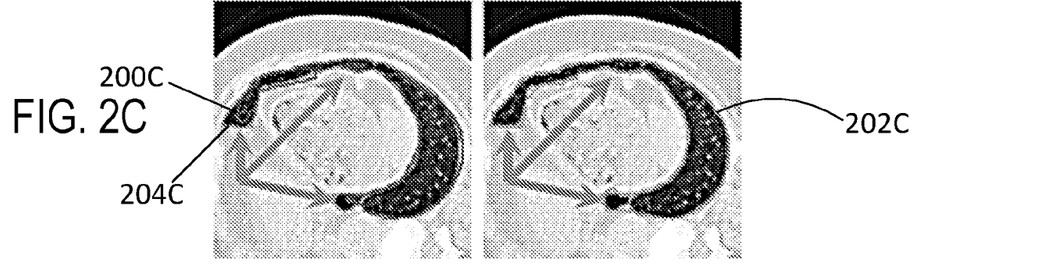
Figure 2D:
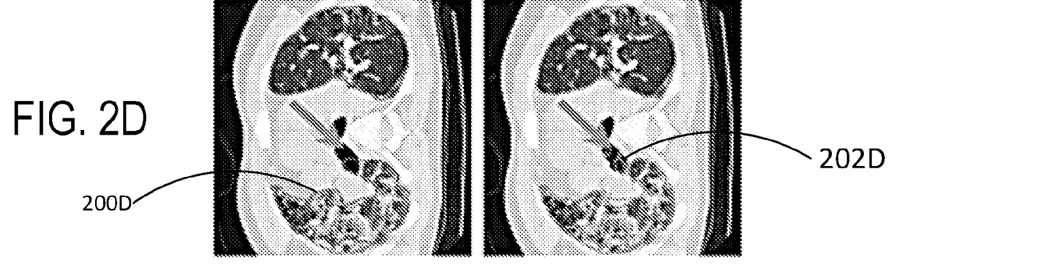
Figure 2E:
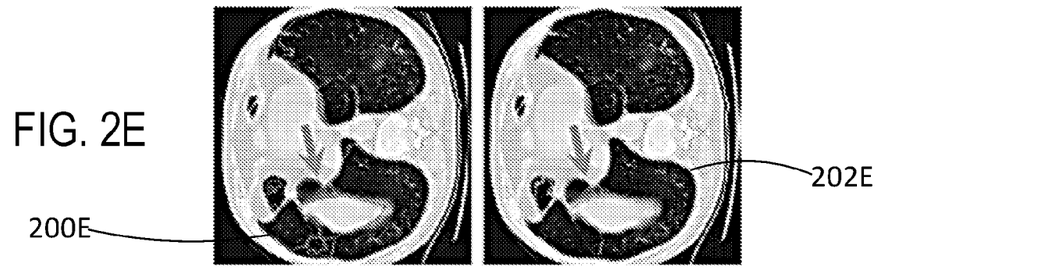

FIGS. 2A-2E depict selected qualitative examples of 2D cross-sections of lungs with image segmentations, demonstrating considerable improvements in the visual quality and usefulness of PLS masks. Example masks 200A-200E of HNN are shown in the left column example masks 202A-202E of P-HNN according to the implementation example are shown in the right column, respectively. Ground truth masks 204A-204E are also shown. As seen in FIG. 2A, the HNN approaches exhibit difficulties in producing the image segmentation mask 200A of the pulmonary bullae (indicated with arrows), whereas the P-HNN mask 202A captures it. As shown in FIG. 2B, part of the pleural effusion (indicated with arrows) is erroneously included by HNN in the mask 200B, while the part of pleural effusion is left out of the P-HNN lung mask 202B. In FIG. 2C, the P-HNN implementation example is shown to be better able to capture finer details in the lung mask 202C, as compared to the HNN lung mask 200C. In the failure case shown in FIG. 2D, both HNN and P-HNN erroneously include the right main bronchus in their respective masks 200D, 202D; however, P-HNN better captures infiltrate regions (indicated with arrows). In FIG. 2E, an example of an erroneous ground-truth 204E, which was filtered out, fails to include a portion of the right lung (indicated with arrows). Both HNN and P-HNN capture the region with the respective masks 200E, 202E, but P-HNN provides a more accurate segmentation of the rest of the lung.

Figure 3A:
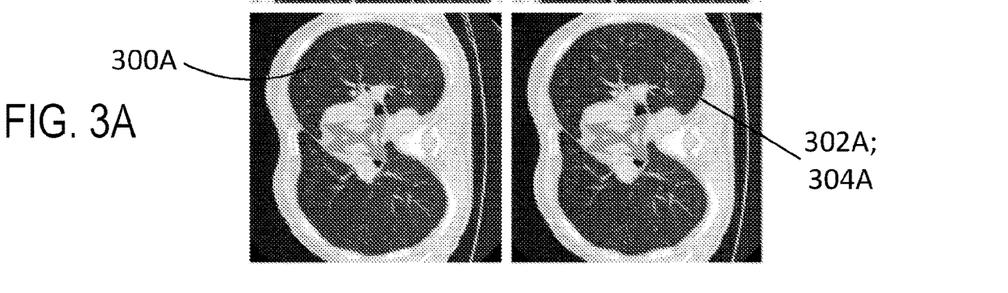
FIGS. 3A-3E are images of mask outputs of non-deep learning approaches and progressive holistically nested network examples.
Figure 3B:
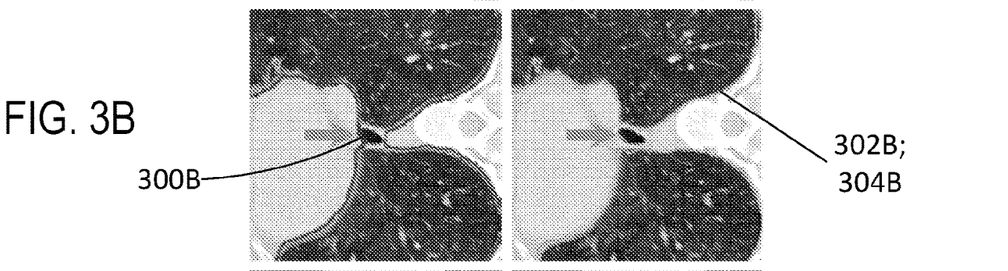
Figure 3C:
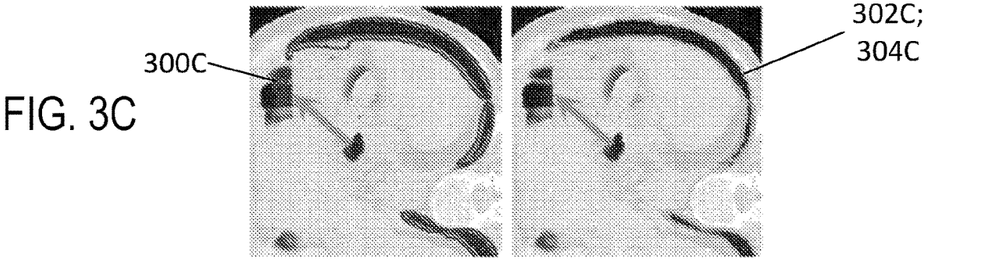
Figure 3D:
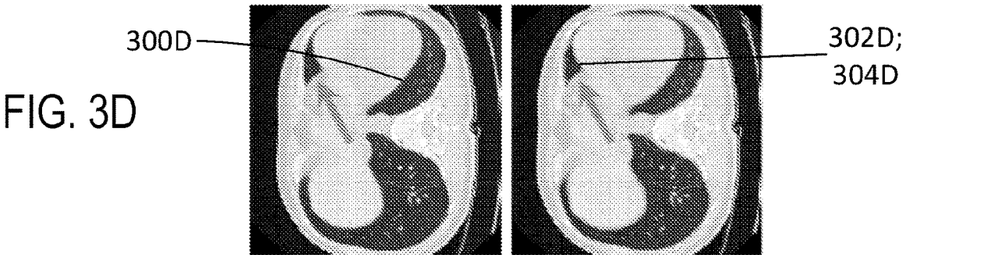
Figure 3E:
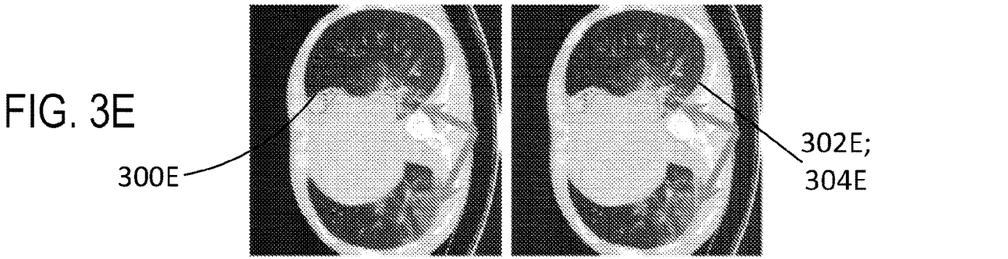

In FIGS. 3A-3E, example masks 300A-300E are shown from Mansoor et al.'s non-deep learning method (Mansoor, A., Bagci, U., Xu, Z., Foster, B., Olivier, K. N., Elinoff, J. M., Suffredini, A. F., Udupa, J. K., Mollura, D. J.: A generic approach to pathological lung segmentation. IEEE Trans. on Medical Imaging 33 (12), 2293-2310 (2014)) and example masks 302A-302E produced with the P-HNN implementation example are shown. Ground truth masks 304A-304E are also shown. As shown in FIG. 3A, P-HNN successfully produces the image segmentation mask 302A of a lung while the mask 300A produced with the non-deep learning approach is unable to match the ground truth mask 304A (indicated with arrows). In FIGS. 3B-3C, it can be seen that the masks 300B, 300C leak into the esophagus and intestine, respectively. The mask 300D in FIG. 3D does not fully capture the lung field (indicated with arrows), while the mask 302D produced with P-HNN does not exhibit this problem. As shown in FIG. 3E, the mask 302E produced with the P-HNN implementation is much better able to capture regions with ground-glass opacities (indicated with arrows) than the mask 300E.

Figure 4A:
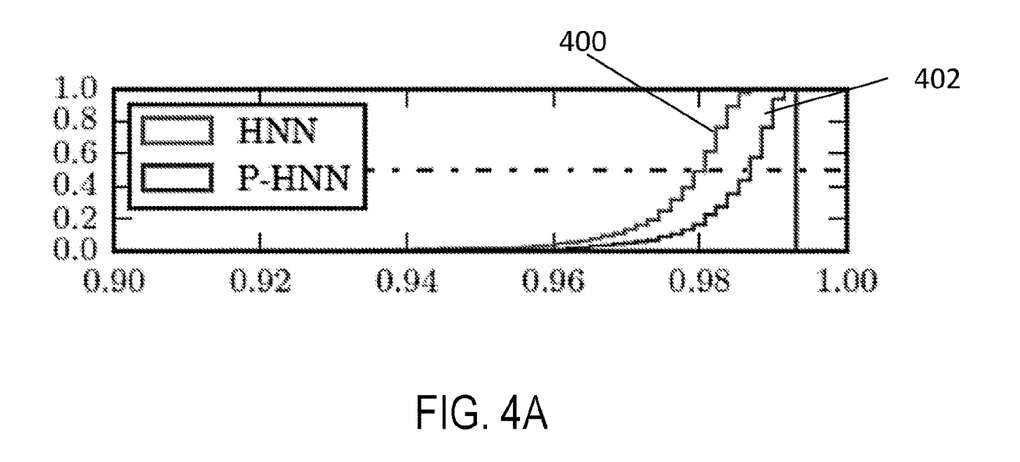
FIG. 4A-4B are cumulative histograms comparing progressive holistically nested network examples with holistically nested network and non-deep learning approaches.
Figure 4B:
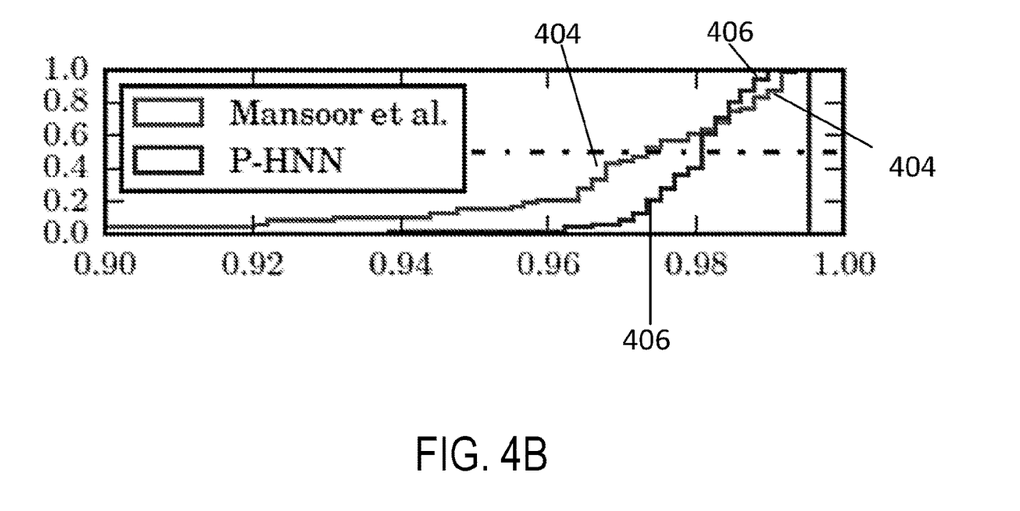

FIG. 4A depicts cumulative histograms 400, 402 of Dice scores for the HNN approach and the P-HNN implementation example, respectively. As shown, the multi-path enhancement of P-HNN significantly ($p<0.001$) and consistently enhances segmentation performance over HNN. FIG. 2 depicts selected qualitative examples, demonstrating considerable improvements in the visual quality and usefulness of PLS masks. FIG. 4B shows cumulative histograms 404, 406 of Dice scores for the Mansoor et al. PLS tool and the P-HNN implementation example, respectively, on a subset of 47 cases with infectious diseases. Differences in score distributions were statistically significant ($p<0.001$) for both FIGS. 4A and 4B using the Wilcox signed-rank test.

Table 1(a) below depicts the mean 3D Dice score (DS) and volumetric similarity (VS), along with standard deviation, of HNN versus the P-HNN implementation example, under 5-fold cross validation. As can be seen, while standard HNN posts very high mean DSs of 0.978, the P-HNN implementation example is able to outperform the HNN, posting even higher average DSs of 0.985. Table 1(b) depicts P-HNN scores as compared with non-deep learning approach by Mansoor et al., using 47 volumes from the NIH dataset. The Mansoor et al. approach has recently reported state-of-the-art performance on challenging and varied infectious disease CT scans. As Table 1(b) and FIG. 4B illustrate, P-HNN significantly outperforms the Mansoor et al. approach, producing much higher DSs.

TABLE 1(a)

| Dataset | Model | DS | VS |
| --- | --- | --- | --- |
| LTRC | HNN | 0.980 ± 0.006 | 0.994 ± 0.005 |
|  | P-HNN | 0.987 ± 0.005 | 0.995 ± 0.004 |
| UHG | HNN | 0.971 ± 0.010 | 0.992 ± 0.009 |
|  | P-HNN | 0.979 ± 0.010 | 0.993 ± 0.007 |
| NIH | HNN | 0.962 ± 0.032 | 0.982 ± 0.028 |
|  | P-HNN | 0.969 ± 0.034 | 0.984 ± 0.021 |
| Total | HNN | 0.978 ± 0.013 | 0.992 ± 0.010 |
|  | P-HNN | 0.985 ± 0.011 | 0.994 ± 0.008 |

TABLE 1(b)

| Model | DS | VS |
| --- | --- | --- |
| Mansoor et al. | 0.966 ± 0.036 | 0.975 ± 0.037 |
| P-HNN | 0.980 ± 0.009 | 0.993 ± 0.006 |

The P-HNN implementation example and other examples herein can provide deep-learning tools for PLS that combine the powerful concepts of deep supervision and multi-path connections within the fully convolutional neural network setting. In representative examples, coarsening resolution problems associated with convolutional neural networks are addressed using a progressive multi-path enhancement. Unlike other approaches, in many embodiments herein, progressive holistically nested convolutional neural networks require no extra parameters and even fewer parameters than standard HNNs. After testing on 929 thoracic CT scans exhibiting infection-, ILD-, and COPD-based pathologies, the largest evaluation of PLS to-date, P-HNN examples herein consistently outperform typical HNN approaches, producing mean DSs of $0.985 \pm 0.011$ ($p<0.001$). Also, compared against a non-deep learning PLS tool, P-HNN examples can also provide significantly improved segmentation masks. Thus, these results demonstrate that the progressive multi-path enhancement of P-HNN examples provides a less complex, yet highly effective, way to produce robust PLS masks. P-HNN examples can also be applied to pathological lungs with other morbidities, e.g., tumors or cancer, and could provide a straightforward and powerful tool for other segmentation tasks.

Other Examples

Figure 5:
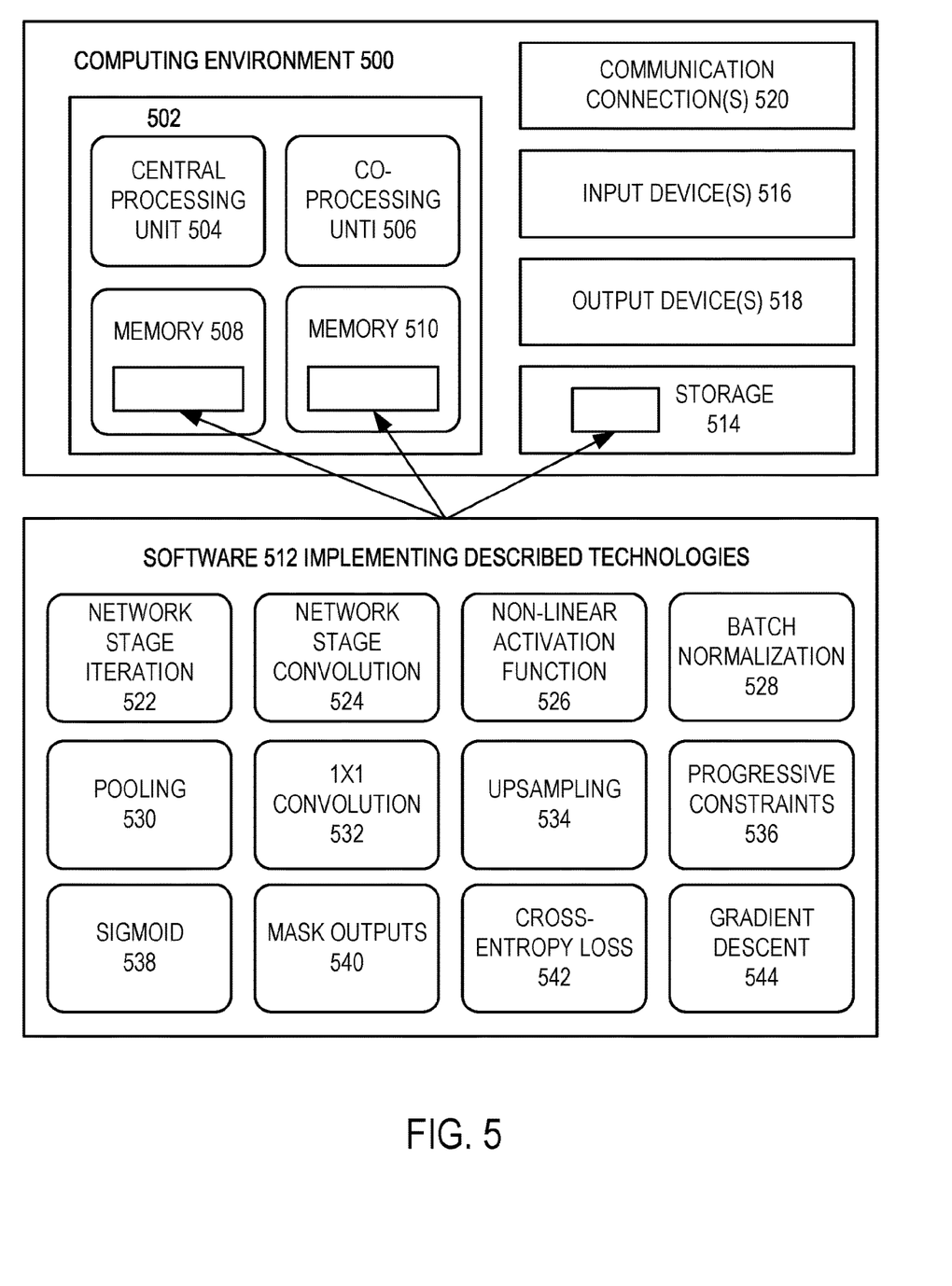
FIG. 5 is schematic of an example progressive holistically nested network computing environment.

FIG. 5 shows a representative computing environment 500 which can implement method steps and algorithms described herein for image segmentation systems and components. The computing environment 500 is shown in general form and is not intended to suggest a limitation on any specific use or functionality, as various examples or portions of examples herein can be implemented in general purpose or special purpose computing systems, including desktop computers, tablet computers, mobile devices, hand-held devices, dedicated processors, mainframe computers, minicomputers, multi-processor systems, MCUs, PLCs, ASICs, FPGAs, CPLDs, systems on a chip, imaging devices using various modalities (including but not limited to CT scanners, MRI scanners, ultrasound devices, echocardiography devices, radiography devices, photoacoustic devices, electrical impedance tomography devices, non-medical imaging devices, etc.), etc. The computing environment 500 includes a core grouping of computing components 502 that includes one or more processing units 504, 506 and memory 508, 510. In some examples, processing units can be configured based on RISC or CSIC architectures, and can include one or more general purpose central processing units, application specific integrated circuits, graphics or co-processing units or other processors. In representative examples, high-end graphics processing units are used to train convolutional neural networks. In some examples, multiple core groupings of computing components 502 can be distributed among image analysis modules, and various modules of software 512 can be implemented separately on separate computing devices.

The memory 508, 510 can be volatile memory (e.g., registers, cache, RAM), non-volatile memory (e.g., ROM, EEPROM, flash memory, etc.), or a combination of volatile and non-volatile memory. The memory 508, 510 is generally accessible by the processing units 504, 506 and can store the software 512 in the form computer-executable instructions that can be executed by the one or more processing units 504, 506 coupled to the memory 508, 510. The computing environment 500 can also include storage 514, input and output devices or ports 516, 518, and communication connections 520. The storage 514 can be removable or non-removable and include magnetic media, CD-ROMS, DVDs, or any other medium that can be used to store information in a non-transitory way and which can be accessed within the computing environment 500. In typical examples, the storage 514 can store instructions for the software 512 implementing one or more method steps and algorithms described herein.

Input and output devices and ports 516, 518 can include imaging devices (e.g., MRI devices, CT devices, etc.), devices storing imaging data, etc. Various interconnections can be included, such as one or more buses, controllers, routers, switches, etc., that can couple various components of the computing environment 500 and imaging devices or image data storing devices together. The communication connections 520 and the input and output ports 516, 518 enable communication over a communication medium to various imaging system components, including other imaging system computing devices, and external system components and computing devices. The communication medium, such as electrical, optical, RF, etc., can convey information such as computer-executable instructions, 3D image data, 2D image data, 1D image data, convolutional network stage information, such as parameters, image segmentation data, mask outputs, or other data in a modulated data signal. A modulated data signal can include signals having one or more of characteristics (e.g., frequency, amplitude, duty cycle, etc.) set or changed so as to encode information in the signal.

The software 512 can include one or more software modules or programs, including convolutional network stage processing and iteration software module 522 that can direct input image data through multiple network stages of a progressive holistically nested convolutional neural network to produce image segmentations of selected targets in the input image data. At each network stage, image data is processed through one or more convolution layers with network stage convolution module 524 that scan or slide a set of trainable network parameter weights across the image data to produce a convolution layer output. Also at each network stage, the convolved image data output is processed through a non-linear activation function 526 that allows training and deep supervision. Each network stage can use a batch normalization routine 528 that normalizes network stage outputs. Batch normalization assists with training by improving convergence (e.g., reducing training time), reduce variance between training image sets, and simplifying initial convolution layer network parameter selection. The software 512 can also include a pooling module 530 that can be used at one or more of the network stages (though typically not the last). The pooling module 530 typically receives outputs from the non-linear activation function 526 and downsamples the spatial extent of the output data slices by discarding selected activations, typically without varying a depth of the output data.

Side outputs are formed at the various network stages by processing the outputs of the non-linear activation function 526 through a series of side stages and are used to progressively improve a final mask output of the convolutional neural network. For example, a side output can be processed through a 1×1 convolution module 532 that typically provides a dimensionality reduction in the depth of the side output. Typically, deeper stages probe deeper scales resulting resolution changes in the image data. After the first stage, which typically retains an original resolution of the image data, the 1×1 convolved side output can be processed through an upsampling module 534 that upsamples the side output to the original resolution. A progressive constraints module 536 can store progressive constraints associated with the convolutional neural network that force improvements at each network in producing the final mask output corresponding to the output image segmentation of the processed image data. In representative examples, the progressive constraint forces a simple addition of the 1×1 convolved and upsampled activations of the current stage with the previous one before applying a sigmoid function with a sigmoid module 538. The outputs of the sigmoid function at each of the stages can correspond to mask outputs 540 for the respective stages. During training of the convolutional neural network, a cross-entropy loss module 542 determines a loss at each side output, and a gradient descent module 544 is used to backpropagate differences between training image ground truths and the mask outputs 540, including the losses determined by the cross-entropy loss module 542, to update network parameter weights at the different network stages. During prediction, various training-oriented modules can be disabled or omitted, including various optimizers, as network weights are typically settled. The various algorithms herein may be, for example, embodied as software or firmware instructions carried out by a digital computing unit or device.

Figure 6:
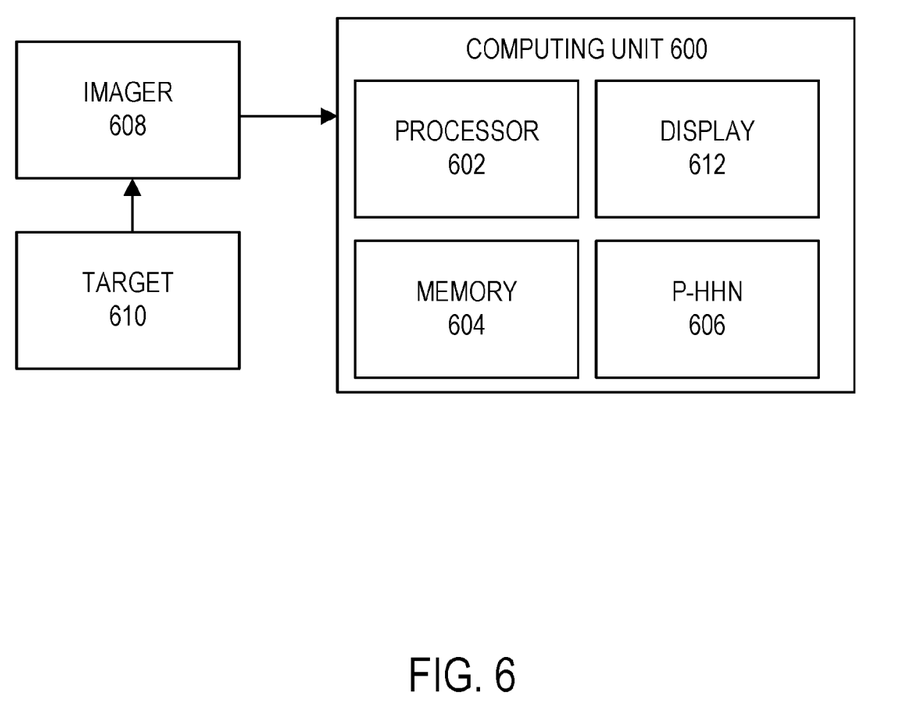
FIG. 6 is a schematic of an example system for progressive holistically nested network image segmentation.

FIG. 6 is a computing unit 600, computer, or other processing system comprising a processor 602 and memory 604, such as a personal computer, a workstation, a mobile computing device, or a networked computer, can be used to perform the disclosed herein, including any combination of CT or MR imaging acquisition, imaging processing, imaging data analysis, data storage, and output/display of results (e.g., segmentation maps, etc.) based on progressive holistically nested convolutional neural networks 606. For example, an imaging device 608 can be coupled to the computing unit 600 and configured to obtain images, such as 2D or 3D images, of a target, such as an anatomical or non-anatomical target 610. The computer or processing system may include a hard disk, a removable storage medium such as a floppy disk or CD-ROM, and/or other memory such as random access memory (RAM). Computer-executable instructions for causing a computing system to execute the disclosed methods can be provided on any form of tangible and/or non-transitory data storage media, and/or delivered to the computing system via a local area network, the Internet, or other network. Any associated computing process or method step can be performed with distributed processing. For example, extracting information from the imaging data and determining and/or producing image segmentation maps can be performed at different locations and/or using different computing systems. Some embodiments can include a display 612 that can be configured to display image segmentation outputs of the target 610 based on image processing through one or more of the progressive holistically nested convolutional neural networks 606.

Figure 7:
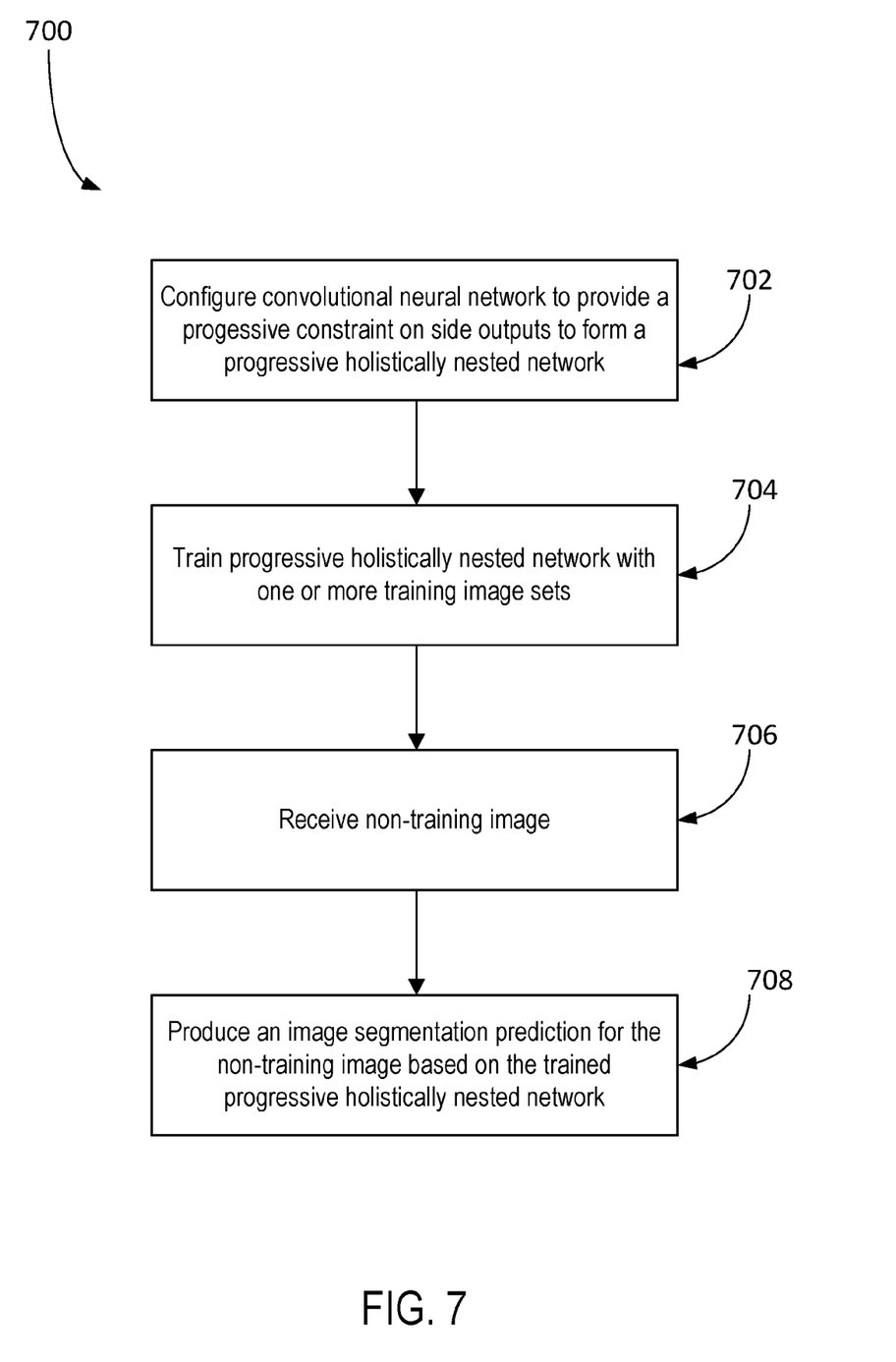
FIG. 7 is a flowchart of a progressive holistically nested network method.

FIG. 7 shows an example method 700 of using a convolutional neural network. At 702, a convolutional neural network is configured to provide a progressive constraint on side outputs of various network stages to form a progressive holistically nested network. At 704, the progressive holistically nested convolutional neural network is trained with one or more training image sets. At 706, a non-training image is received, such as from a CT system, MRI system, or another imager or imaging system. At 708, an image segmentation prediction is produced for the non-training image based on the trained progressive holistically nested network.

Figure 8:
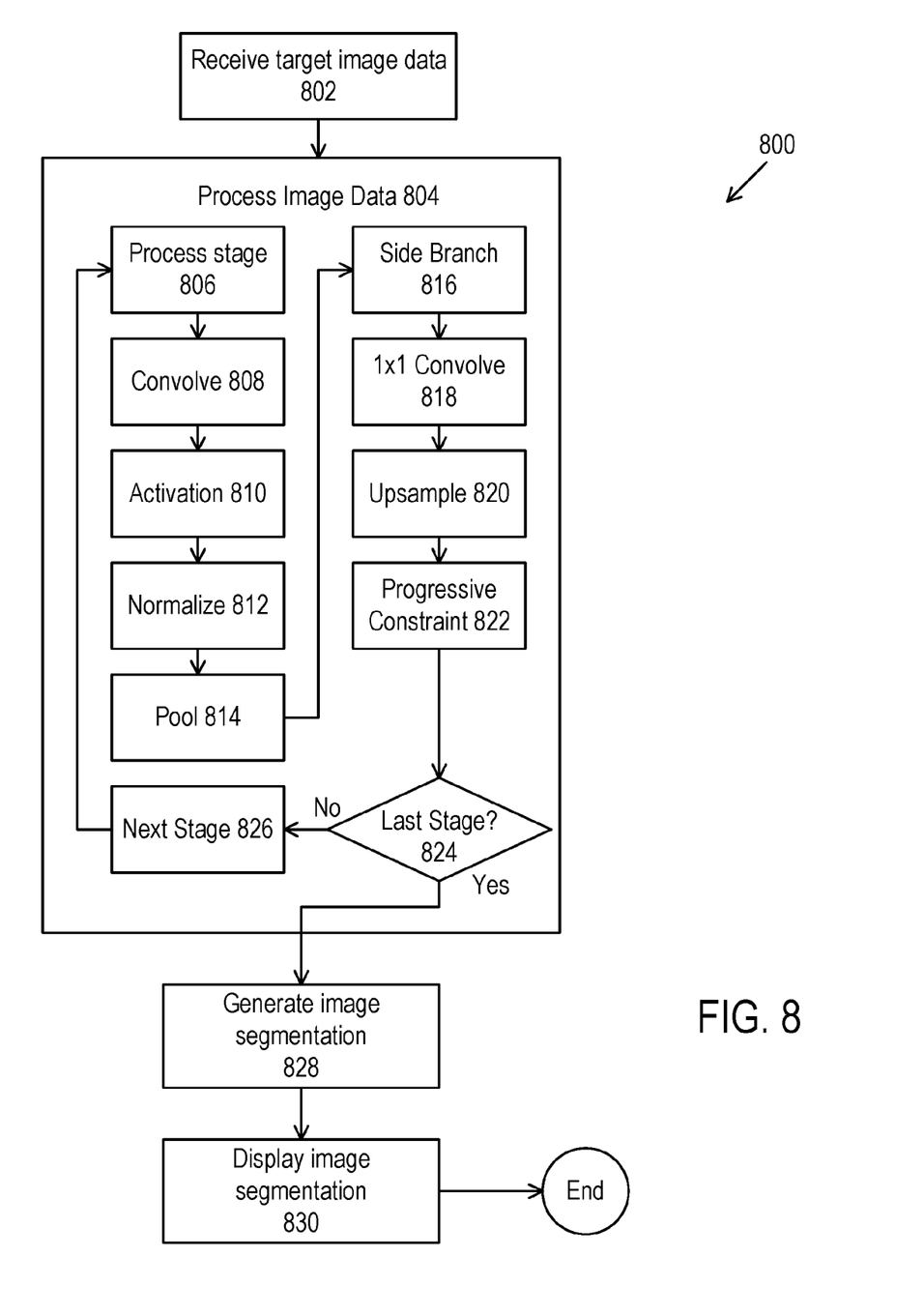
FIG. 8 is a flowchart of a method of image segmentation prediction using a progressive holistically nested network.

FIG. 8 shows an example method 800 of processing image data to make an image segmentation prediction for a target. At 802, target image data is received, such as that associated with non-training anatomical target (e.g., lung, brain, heart, colon, etc.) or a non-training non-anatomical target. At 804, the image data is processed with a progressive holistically nested convolutional neural network (P-HNN) through multiple network stages. For example, at 806 the P-HNN begins processing of the image data through a network stage. At 808, the image data at the current network stage is convolved using convolution operation with selected weights. At 810, an activation function is applied to the convolved data. At 812, the convolved data is normalized, and then pooled at 814 through a neural network pooling layer. A side branch is formed for the network stage at 816. The side branch activation is convolved with a 1×1 convolution at 818. For network stages after an initial one or a first one, the convolved data is upsampled at 820, and a progressive constraint is applied at 822. Example progressive constraints can include summing the convolved upsampled output with the convolved, upsampled, and progressively summed output from the preceding stage (if the preceding stage is not the first stage) or summing the convolved upsampled output with the convolved output of the preceding stage (if the preceding stage is the first stage). Other progressive constraints can be applied to form multi-path connections, including other operations (e.g., multiplication, convolutions, etc.). Also, selected stages can be skipped or excluded from a progressively constrained stage sequence, such as stages that do not produce a side output. A check 824 is performed to determine if the last stage of the P-HNN is reached, and if the last has not been reached, the stage number is increased by one at 826 and the processing of the next stage begins again at 806. If the last stage is reached, then at 828 an image segmentation associated with the image data is generated typically by applying a sigmoid function to the progressively created side output. At 830, the image segmentation overlaid on the original image associated with the image data can be displayed.

Figure 9:
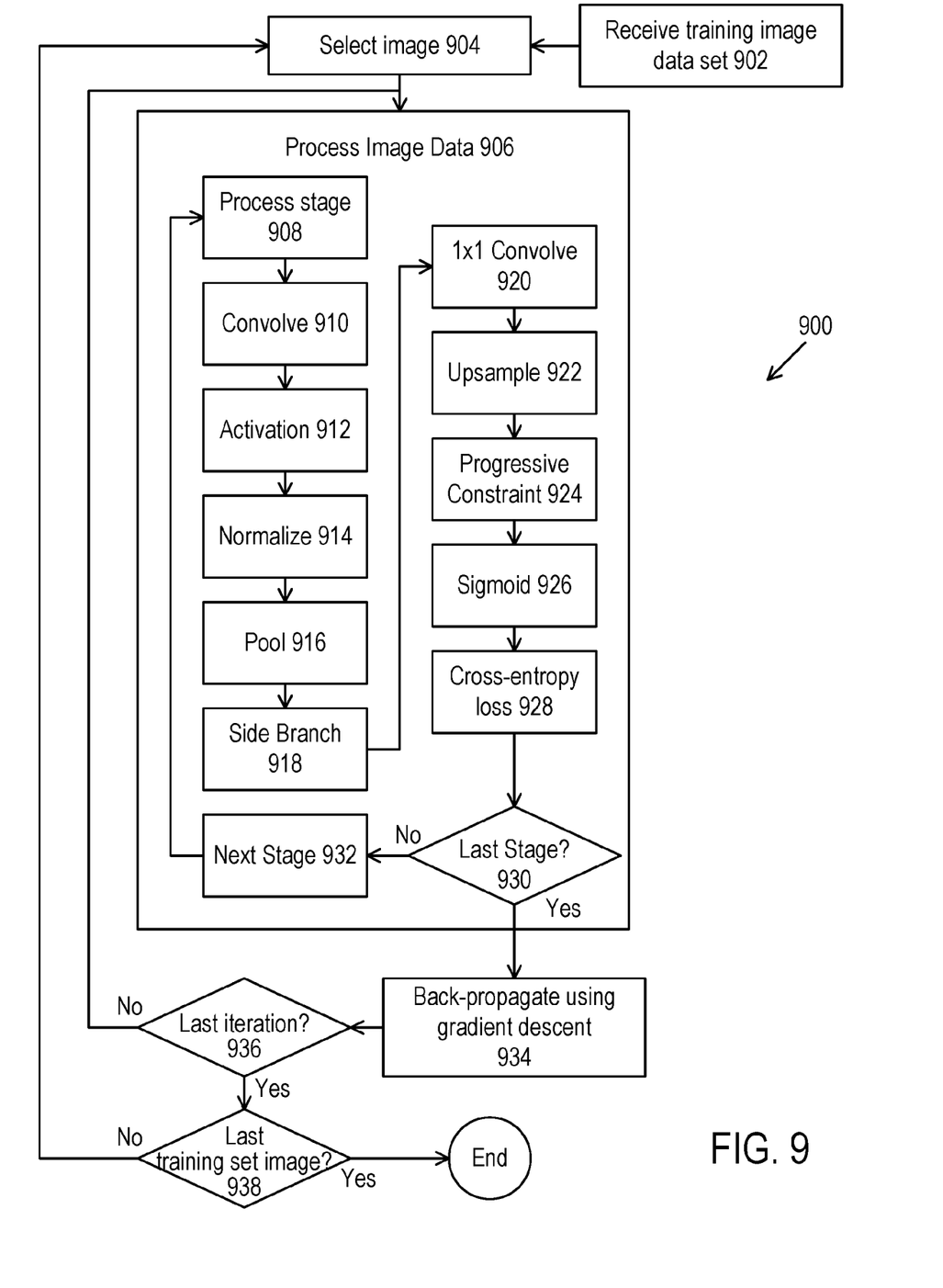
FIG. 9 is a flowchart of a method of image segmentation training of a progressive holistically nested network.

FIG. 9 shows an example method 900 of training a P-HNN. At 902, a set of training images is received and at 904 one of the training images is selected for training the P-HNN. At 906, the selected training image is image-processed through the P-HNN. For example, at 908, the P-HNN begins processing of the image data through a network stage. At 910, the image data at the current network stage is convolved using convolution operation with selected weights. At 912, an activation function is applied to the convolved data. At 914, the convolved data is normalized, and then pooled at 916 through a neural network pooling layer. A side branch is produced for the network stage at 918. The side branch activation is convolved with a 1×1 convolution at 920. For network stages after an initial one or a first one, the convolved data is upsampled at 922, and a progressive constraint is applied at 924. A sigmoid is applied to the progressively created side output at 926. A comparison between the mask output and a ground truth mask is performed, and an associated cross-entropy loss is calculated at 928. A check 930 is performed to determine whether the last stage of the P-HNN has been reached, and if the last has not been reached, the stage number is increased by one at 932 and the processing of the next stage begins again at 908. If the last stage has been reached, a back-propagation 934 through the P-HNN is performed through gradient descent and the weights for the different network stages are updated based on the cross-entropy losses. At 936, a check is performed to determine if the last training iteration for the current training image has been reached, and if has not, the processing of the image data is performed again at 906. If the last iteration has been reached, then a check to determine if the last training set image has been selected is performed at 938. If the last training set image has not been selected, then a new image is selected at 904 and the subsequent training is performed on the new image at 906. In this way, a complete set of training images can be used to train the P-HNN.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any embodiments disclosed in this application. The invention extends to any novel one, or any novel combination, of the features disclosed in this application, or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the figures of this application may not show the various ways in which the disclosed methods can be used in conjunction with other methods.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims.

The invention claimed is:

1. A method, comprising:
processing image data through a plurality of network stages of a progressively holistically nested convolutional neural network;
wherein the processing the image data includes producing a side output from a network stage m, of the network stages, where m>1, based on a progressive combination of an activation output from the network stage m and an activation output from a preceding stage m−1.

2. The method of claim 1, wherein the progressive combination is an addition of the activation output of the network stage m and the activation output of the network stage m−1.

3. The method of claim 1, wherein the convolutional neural network includes at least three sequential network stages.

4. The method of claim 1, wherein each network stage includes a plurality of layers including at least a convolutional layer, a nonlinear activation layer, batch normalization layer, and a pooling layer, except a last network stage that does not include a pooling layer.

5. The method of claim 1, wherein the image data comprises a 2D section image of 3D medical imaging data, the method further comprising:
generating an image segmentation of an image feature in the 2D section image, the image segmentation corresponding to a mask output of a last stage of the multi-stage convolutional neural network that is based on a progressively created side output of the last stage.

6. The method of claim 1, further comprising training the convolutional neural network through deep supervision at each network stage by processing a set of a plurality of input training images, having respective ground truth image segmentations, through the network stages.

7. The method of claim 6, wherein the training comprises for each input training image:
determining a cross-entropy loss at each network stage associated with a side output of the network stage using a class-balancing weight corresponding to an average of image segmentation edge ground truths over the set of input training images;
producing an image segmentation estimate at each network stage corresponding to a mask output of the side output of the network stage; and
back-propagating through the network stages with gradient descent to update network stage parameters of each network stage based on differences between the image segmentation estimates and the ground truth image segmentation of the input training image.

8. The method of claim 1, wherein the method comprises image segmentation of organs, tumors, or other anatomical bodies of a patient based on the image data, and the image data includes a target body.

9. The method of claim 8, wherein the target body is a pathological lung.

10. The method of claim 9, wherein the pathological lung has an infection, interstitial lung disease, or chronic obstructive pulmonary disease.

11. The method of claim 1, wherein the image data is derived from one or more computerized tomography (CT) scans.

12. The method of claim 1, wherein processing the image data comprises classifying individual pixels or patches of the image data.

13. The method of claim 1, wherein producing the side output comprises applying a progressive constraint on multi-scale pathways.

14. The method of claim 13, wherein the progressive constraint on multi-scale pathways requires no additional convolutional layers or network parameters.

15. The method of claim 1, wherein the method comprises image segmentation of a non-anatomical object that is not an organ, tumor, or anatomical body, and the segmentation is based on natural images and not 3D medical imaging.

16. A computing system comprising a processor and memory, the system operable to implement the method of claim 1.

17. One or more non-transitory computer readable media storing computer-executable instructions, which when executed by a computer cause the computer to perform the method of claim 1.

18. A system comprising:
a 3D imaging system operable to obtain 3D imaging data for a patient including a target anatomical body; and
a computing system comprising a processor, memory, and software, the computing system operable to:
process the 3D imaging data through a plurality of progressively holistically nested convolutional neural network stages of a convolutional neural network, including to produce a side output from a network stage m, of the network stages, where m>1, based on a progressive combination of an activation output from the network stage m and an activation output from a preceding stage m−1; and
generate an image segmentation of the target anatomical body based on a progressively created mask output of a last network stage of the network stages.

19. The system of claim 18, wherein the target anatomical body is a pathological lung.

20. The system of claim 19, wherein the pathological lung has an infection, interstitial lung disease, or chronic obstructive pulmonary disease.

21. The system of claim 18, wherein the 3D imaging system comprises a computerized tomography system and the 3D imaging data is derived from one or more computerized tomography scans.

22. The system of claim 18, wherein the computing system is operable to classify individual pixels or patches of the 3D imaging data in a bottom-up approach.

23. The system of claim 18, wherein the computing system is operable to apply a progressive constraint on multi-scale pathways.

24. The system of claim 23, wherein the progressive constraint on multi-scale pathways requires no additional convolutional layers or network parameters.

25. The system of claim 18, wherein the progressive combination is an addition of the activation output of the network stage m and the activation output of the network stage m−1.

26. The system of claim 18, wherein the computing system is operable to train the convolutional neural network through deep supervision at each network stage by processing a set of a plurality of input training images, having respective ground truth image segmentations, through the network stages.

27. The system of claim 26, wherein the computing system is operable to provide the training by, for each input training image:
- determining a cross-entropy loss at each network stage associated with a side output of the network stage using a class-balancing weight corresponding to an average of image segmentation edge ground truths over the set of input training images;
- producing an image segmentation estimate at each network stage corresponding to a mask output of the side output of the network stage; and
- backpropagating through the network stages with gradient descent to update network stage parameters of each network stage based on differences between the image segmentation estimates and the ground truth image segmentation of the input training image.

\* \* \* \* \*